(12) United States Patent
Hayman

(10) Patent No.: US 9,840,911 B2
(45) Date of Patent: Dec. 12, 2017

(54) CEMENT EVALUATION

(71) Applicant: SCHLUMBERGER TECHNOLOGY CORPORATION, Sugar Land, TX (US)

(72) Inventor: Andrew J. Hayman, Voisins-le-Bretonneux (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 206 days.

(21) Appl. No.: 14/780,562

(22) PCT Filed: Mar. 27, 2014

(86) PCT No.: PCT/US2014/031930
§ 371 (c)(1),
(2) Date: Sep. 28, 2015

(87) PCT Pub. No.: WO2014/160817
PCT Pub. Date: Oct. 2, 2014

(65) Prior Publication Data
US 2016/0061029 A1     Mar. 3, 2016

Related U.S. Application Data

(60) Provisional application No. 61/806,395, filed on Mar. 28, 2013.

(30) Foreign Application Priority Data

Mar. 28, 2013   (EP) ..................................... 13305406

(51) Int. Cl.
*E21B 49/00*     (2006.01)
*E21B 47/00*     (2012.01)
(Continued)

(52) U.S. Cl.
CPC ........ *E21B 49/005* (2013.01); *E21B 47/0005* (2013.01); *G01N 33/383* (2013.01); *G01V 1/48* (2013.01); *G01V 1/50* (2013.01)

(58) Field of Classification Search
CPC . E21B 49/005; E21B 47/0005; G01N 33/383; G01V 1/48; G01V 1/50
See application file for complete search history.

(56) References Cited

U.S. PATENT DOCUMENTS 6,041,861 A    3/2000  Mandal et al.
6,050,141 A    4/2000  Tello et al.
(Continued)

OTHER PUBLICATIONS

International Search Report and Written Opinion issued in related International Application No. PCT/US2014/031930 dated Oct. 13, 2014.
(Continued)

*Primary Examiner* — Paul West
(74) *Attorney, Agent, or Firm* — Michael Dae

(57) ABSTRACT

Surface equipment of a cement analysis system (CAS) estimates a first drilling fluid slowness (FSLO) and a first drilling fluid acoustic impedance (ZMUD) based on a type and density of wellbore drilling fluid. A second FSLO is estimated based on a thickness and diameter of wellbore casing and transit time for energy emitted by a downhole tool to travel to and from the casing. An FSLO graphical interface is generated based on the first and second FSLO. A second ZMUD is estimated based on the drilling fluid type and density and one of the first and second FSLO selected utilizing the FSLO graphical interface. A ZMUD graphical interface is generated based on the first and second ZMUD. The downhole tool then obtains log data utilizing at least one parameter selected utilizing the ZMUD graphical interface. The log data includes a final ZMUD measured with respect to wellbore depth.

20 Claims, 11 Drawing Sheets

(51) Int. Cl.
*G01V 1/50* (2006.01)
*G01N 33/38* (2006.01)
*G01V 1/48* (2006.01)

(56) References Cited

U.S. PATENT DOCUMENTS

| | | |
|---|---|---|
| 2006/0067162 A1 | 3/2006 | Blankinship et al. |
| 2006/0133205 A1 | 6/2006 | Van Kuijk et al. |
| 2013/0075158 A1* | 3/2013 | Johnson .................. G01V 1/44 |
| | | 175/48 |

OTHER PUBLICATIONS

Hayman et al., "High-resolution Cementation and Corrosion Imaging by Ultrasound", SPWLA 32nd Annual Logging Symposium, Jun. 16-19, 1991, pp. 1-25.

Hayman, "Ultrasonic Properties of Oil-Well Drilling Muds", 1989 IEEE Ultrasonics Symposium, Paper PE-1, pp. 327-332.

Van Kuijk et al., "A Novel Ultrasonic Cased-Hole Imager for Enhanced Cement Evaluation", IPTG 10546 presented at the International Petroleum Technology Conference in Doha, Qatar, Nov. 21-23, 2005, pp. 1-14.

* cited by examiner

CEMENT EVALUATION

BACKGROUND OF THE DISCLOSURE

The integrity of the cement sheath around a well casing may be evaluated using logging tools, such as acoustic tools that may operate in the 20-100 kHz range and/or ultrasonic tools that may operate in the 0.1 to 1.0 MHz range. Existing ultrasonic imaging (USI) tools may utilize a pulse-echo measurement to stimulate a casing resonance to account for damping affected by the acoustic impedance of the material in the annulus surrounding the casing. Other commercially available tools are operable to obtain flexural attenuation (FA) measurements in addition to pulse-echo measurements, such as may utilize a pitch-catch measurement of flexural wave attenuation along the casing.

SUMMARY OF THE DISCLOSURE

The present disclosure introduces a method in which surface equipment of a cement analysis system (CAS) is operated to estimate a first drilling fluid slowness (FSLO) and a first drilling fluid acoustic impedance (ZMUD) based on a type and density of the drilling fluid. The drilling fluid is in a wellbore extending from a wellsite surface. A steel casing is secured within the wellbore by cement in an annulus between an external diameter of the casing and the wellbore. The surface equipment is disposed at the wellsite surface and comprises a processor. A downhole tool of the CAS is conveyed within the wellbore. The CAS is operated to estimate a second FSLO based on a thickness of the casing, the external diameter, and a transit time for energy emitted by the downhole tool to travel to and from the casing. The CAS is then operated to generate an FSLO graphical interface based on the first FSLO and the second FSLO. The CAS is then operated to estimate a second ZMUD based on the type and density of the drilling fluid and a selected one of the first FSLO and the second FSLO, wherein the selected one of the first FSLO and the second FSLO is selected utilizing the FSLO graphical interface. The CAS is then operated to generate a ZMUD graphical interface based on the first ZMUD and the second ZMUD. The downhole tool is then conveyed within the wellbore while operating the CAS to obtain log data utilizing at least one parameter selected utilizing the ZMUD graphical interface, wherein the log data includes a final ZMUD measured with respect to depth in the wellbore.

The present disclosure also introduces a method in which surface equipment of a cement analysis system (CAS) is operated to estimate a first drilling fluid slowness (FSLO) and a first drilling fluid acoustic impedance (ZMUD) based on a predetermined type and a predetermined density of the drilling fluid. The drilling fluid is in a wellbore extending from a wellsite surface. A steel casing is secured within the wellbore by cement in an annulus between an external diameter of the casing and the wellbore. The surface equipment is disposed at the wellsite surface and comprises a processor. A downhole tool of the CAS is conveyed within the wellbore while operating the CAS to obtain first log data that includes a second FSLO and a second ZMUD each measured with respect to depth in the wellbore. The CAS is then operated to estimate a third FSLO based on a thickness of the casing, the external diameter, and a transit time for energy emitted by the downhole tool to travel to and from the casing. The CAS is then operated to estimate a third ZMUD based on the predetermined density, an expected impedance in the annulus, a selected one of the first FSLO, the second FSLO, and the third FSLO, and a selected one of the first ZMUD, the second ZMUD, and the third ZMUD. The downhole tool is then conveyed in a free-pipe (FP) zone of the wellbore while operating the CAS to obtain second log data that includes a fourth FSLO and a fourth ZMUD each measured with respect to depth in the FP zone. The CAS is then operated to generate an FSLO graphical interface based on the first FSLO, the second FSLO, the third FSLO, and the fourth FSLO. The CAS is then operated to estimate a fifth ZMUD based on the predetermined type and predetermined density of the drilling fluid and a selected one of the first FSLO, the second FSLO, the third FSLO, and the fourth FSLO, wherein the selected one of the first FSLO, the second FSLO, the third FSLO, and the fourth FSLO is selected utilizing the FSLO graphical interface. The CAS is then operated to generate a ZMUD graphical interface based on the first ZMUD, the second ZMUD, the third ZMUD, the fourth ZMUD, and the fifth ZMUD. The downhole tool is then conveyed within the wellbore while operating the CAS to obtain third log data utilizing at least one parameter selected utilizing the ZMUD graphical interface, wherein the third log data includes a final ZMUD measured with respect to depth in the wellbore.

The present disclosure also introduces an apparatus that includes surface equipment disposed at a wellsite surface and comprising a processor, wherein a wellbore extending from the wellsite surface comprises a steel casing secured within the wellbore by cement in an annulus between an external diameter of the casing and the wellbore, and wherein an amount of drilling fluid fills at least a portion of the casing. The surface equipment is operable to estimate a first drilling fluid slowness (FSLO) and a first drilling fluid acoustic impedance (ZMUD) based on a type and density of the drilling fluid. The surface equipment is also operable to estimate a second FSLO based on a thickness of the casing, the external diameter, and a transit time for energy emitted by the downhole tool to travel to and from the casing. The surface equipment is also operable to generate an FSLO graphical interface based on the first FSLO and the second FSLO. The surface equipment is also operable to estimate a second ZMUD based on the type and density of the drilling fluid and a selected one of the first FSLO and the second FSLO, wherein the selected one of the first FSLO and the second FSLO is selected utilizing the FSLO graphical interface. The surface equipment is also operable to generate a ZMUD graphical interface based on the first ZMUD and the second ZMUD. The apparatus also includes a downhole tool operable for conveyance within the drilling fluid inside the wellbore while obtaining log data utilizing at least one parameter selected utilizing the ZMUD graphical interface, wherein the log data includes a final ZMUD measured with respect to depth in the wellbore.

Additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
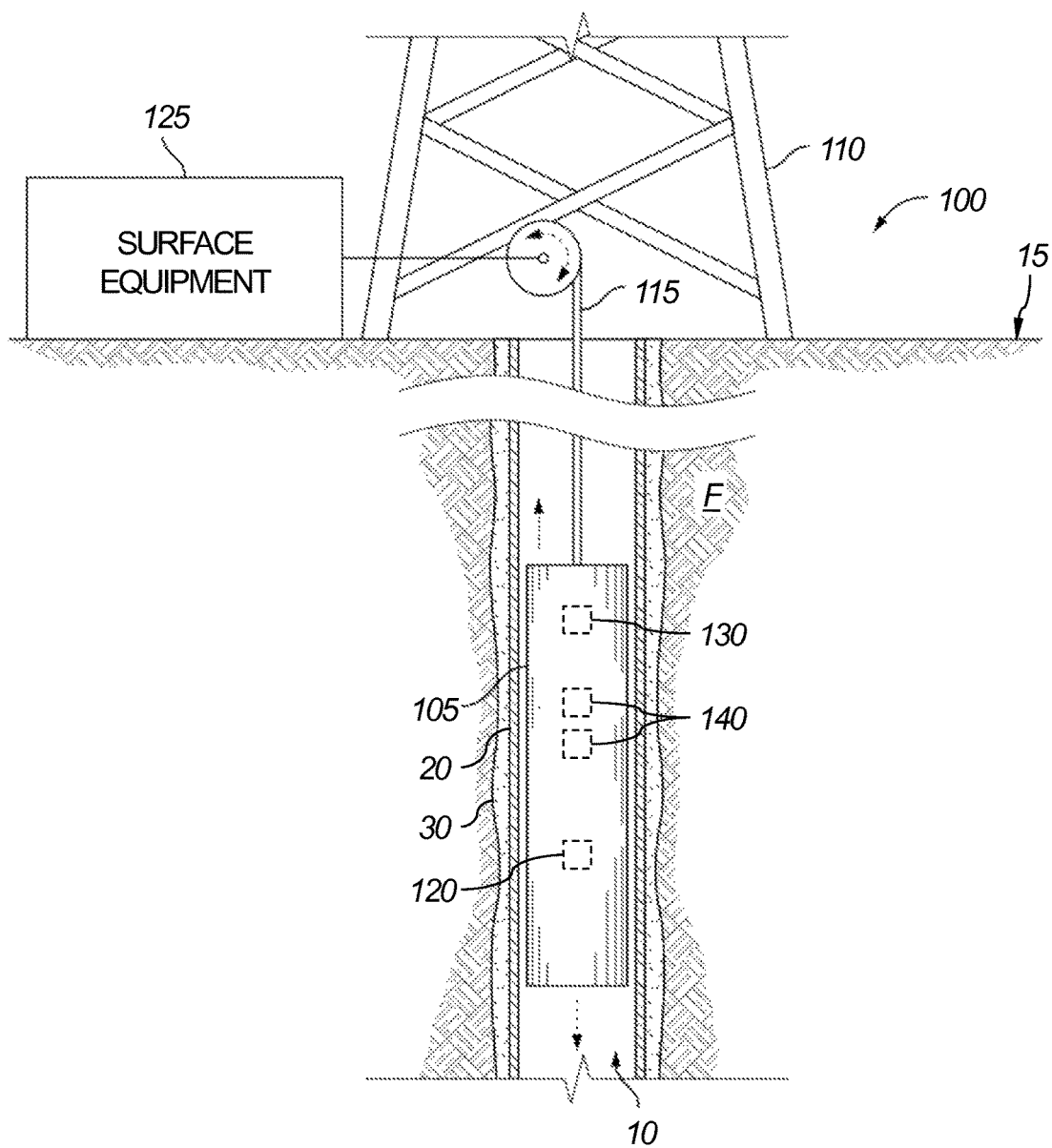
FIG. 1 is a schematic view of at least a portion of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a schematic view of an example cement analysis system (CAS) 100 that may be employed onshore and/or offshore according to one or more aspects of the present disclosure. As depicted in FIG. 1, a downhole tool 105 may be suspended from a rig 110 in a wellbore 10 formed in one or more subterranean formations F. The wellbore 10 includes a casing 20 secured by cement 30 in an annulus defined between an external diameter of the casing 20 and one or more walls of the wellbore 10.

The downhole tool 105 may be or comprise an ultrasonic imager tool operable to scan condition of the casing 20 and/or the bond of the cement 30 around a substantial portion of the circumference of the casing 20 (e.g., 360° azimuthal coverage). The downhole tool 105 may be operable to deliver an accurate, high-resolution, and/or comprehensive real-time confirmation of the impedance of the material in the annulus that is indicative of cement quality and bond, downhole casing conditions, and casing inspection and monitoring applications including, for example, corrosion detection, identification of internal and external damage or deformation, and casing thickness analysis for collapse and burst pressure calculations, among others within the scope of the present disclosure.

The downhole tool 105 may be or comprise one or more of an acoustic tool, a formation evaluation tool, a magnetic resonance tool, a monitoring tool, a neutron tool, a nuclear tool, a reservoir characterization tool, a resistivity tool, a seismic tool, a surveying tool, and/or a telemetry tool, although other downhole tools are also within the scope of the present disclosure. The downhole tool 105 may be operable to obtain pulse-echo measurements as well as at least one of fluid property measurements (FPM) and flexural attenuation (FA) measurements, among other measurements, as described below.

The downhole tool 105 may be deployed from the rig 110 into the wellbore 10 via a conveyance means 115, which may be or comprise a wireline cable, a slickline cable, and/or coiled tubing, although other means for conveying the downhole tool 105 within the wellbore 10 are also within the scope of the present disclosure. As the downhole tool 105 operates, outputs of various numbers and/or types from the downhole tool 105 and/or components thereof (one of which is designated by reference numeral 120) may be sent via, for example, telemetry to surface equipment 125 (at the wellsite surface 15), such as may comprise a logging and control system, among other components. Such outputs may also or instead be stored in various numbers and/or types of memories in the downhole tool 105, such as for subsequent recall and/or processing after the downhole tool 105 is retrieved to surface.

Pulse-echo measurements obtained by the downhole tool 105 may be sensitive to the acoustic impedance of drilling fluid (also referred to herein as mud) inside the casing 20, perhaps to an extent that is several times larger than the sensitivity to the cement 30 and/or other material outside the casing 20. Flexural attenuation measurements obtained by the downhole tool 105 may also be susceptible to drift between the surface calibration of the downhole tool 105 and the downhole measurements, such as may be attributable to differences between surface and downhole pressures and temperatures.

Moreover, existing methods for estimating acoustic impedance of the drilling fluid (ZMUD) have shortcomings. For example, existing algorithms that may be suitable for planning purposes may not be suitable for logging purposes. Existing direct downhole fluid impedance measurements may also be affected by contamination and fluid movement between the FPM-down-log and the cement-up-log, and may not be available in large-diameter subs or existing tools. Inversion techniques based on a combination of pulse-echo and flexural attenuation measurements may be suitable if calibrated correctly, but such inversion is not available unless annulus impedance is less than about 3.5 MRayl. Existing theoretical techniques may also rely on data from different entities and weighted empirical corrections, which may thus also be inaccurate. When available, free-pipe (FP) normalization methods are generally the most accurate provided mud composition inside the casing does not vary. Manual techniques also exist, but these are generally based on separate calculations, local experience, or iterative log reprocessing, each of which can be labor intensive and/or inaccurate.

Other, theoretical methods of calculating ZMUD utilize an ultrasonic slowness of the drilling fluid (FSLO) and density as input, and include a normalization factor in weighted muds, but this may also introduce inaccuracy.

One or more aspects of the present disclosure pertain to one or more workflows and/or methods for determining fluid properties and/or calibration factors for evaluating the cement 30 utilizing pulse-echo measurements or combined pulse-echo and flexural attenuation (FA) measurements. One or more of such workflows and/or methods may include independent choice of fluid slowness (FSLO) and/or mud impedance (ZMUD), graphical review of parameters, free-pipe normalization, impedance inversion normalization, theoretical normalization, a graphical interface to create depth-dependent FSLO and ZMUD curves, quality control (QC) presentation of available fluid property curves (e.g., for traceability), and/or tabular summary of fluid properties and FA calibration values utilized to process one or more logs (e.g., for traceability).

Figure 2:
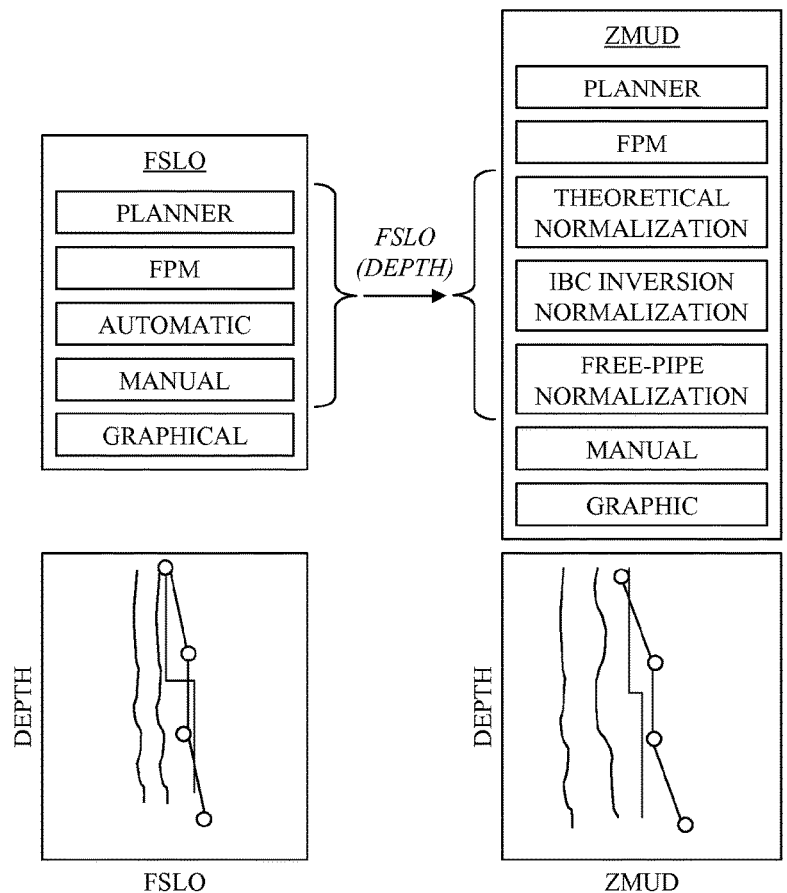
FIG. 2 depicts example methods for obtaining FSLO and ZMUD according to one or more aspects of the present disclosure.

Implementations within the scope of the present disclosure may utilize multiple, perhaps independent methods for determining drilling fluid slowness (FSLO) and mud impedance (ZMUD), as depicted in FIG. 2. For example, referring to FIGS. 1 and 2, collectively, a tool planner associated with the downhole tool 105 (such as may be included in or implemented by the surface equipment 125) may be utilized to estimate FSLO based on density and/or other predetermined parameters of the drilling fluid. FSLO may also or instead be directly measured by the downhole tool 105 or estimated based on one or more such directly measured properties of the drilling fluid (FPM). FSLO may also or instead be estimated, perhaps automatically and/or as a default when other methods are not accurate or available, based on parameters of the casing 20 and/or the downhole tool 105. Example parameters of the casing 20 may include wall thickness and external diameter, among others. Example parameters of the downhole tool 105 may include a transit time for energy emitted by a transducer 130 of the downhole tool 105 to travel to and from the casing 20. FSLO may also or instead be estimated manually, such as may be based on iterative re-processing of log data. FSLO may also or instead be estimated graphically, such as via the FSLO graphical interface described below.

Implementations within the scope of the present disclosure may also utilize multiple methods for determining drilling fluid acoustic impedance (ZMUD). For example, a tool planner associated with the downhole tool 105 (such as may be included in or implemented by the surface equipment 125) may be utilized to estimate ZMUD based on density and/or other predetermined parameters of the drilling fluid. Such a tool planner may be the same tool planner utilized to generate an estimate of FSLO. ZMUD may also or instead be directly measured by the downhole tool 105 or estimated based on one or more such FPM. ZMUD may also or instead be estimated manually, such as may be based on separate calculation, local experience, and/or iterative re-processing of log data. ZMUD may also or instead be estimated graphically, such as via the ZMUD graphical interface described below.

Such methods for estimating ZMUD may be independent of the FSLO estimates described above. However, additional methods for estimating ZMUD may utilize the selected FSLO and Equation (1), set forth below:

$$ZMUD = N * DEN/FSLO \qquad (1)$$

where N is the relevant normalization factor, DEN is the mud density (g/cm$^3$), and FSLO is the selected mud slowness (s/km). For example, a theoretical normalization of ZMUD may be estimated by Equation (2) set forth below, a free-pipe normalization of ZMUD may be estimated by Equation (3) set forth below, and an inversion normalization of ZMUD may be estimated by Equation (4) set forth below:

$$ZMUD = N_{theoretical} * DEN/FSLO \qquad (2)$$

$$ZMUD = N_{free-pipe} * DEN/FSLO \qquad (3)$$

$$ZMUD = N_{inversion} * DEN/FSLO \qquad (4)$$

Figure 3:
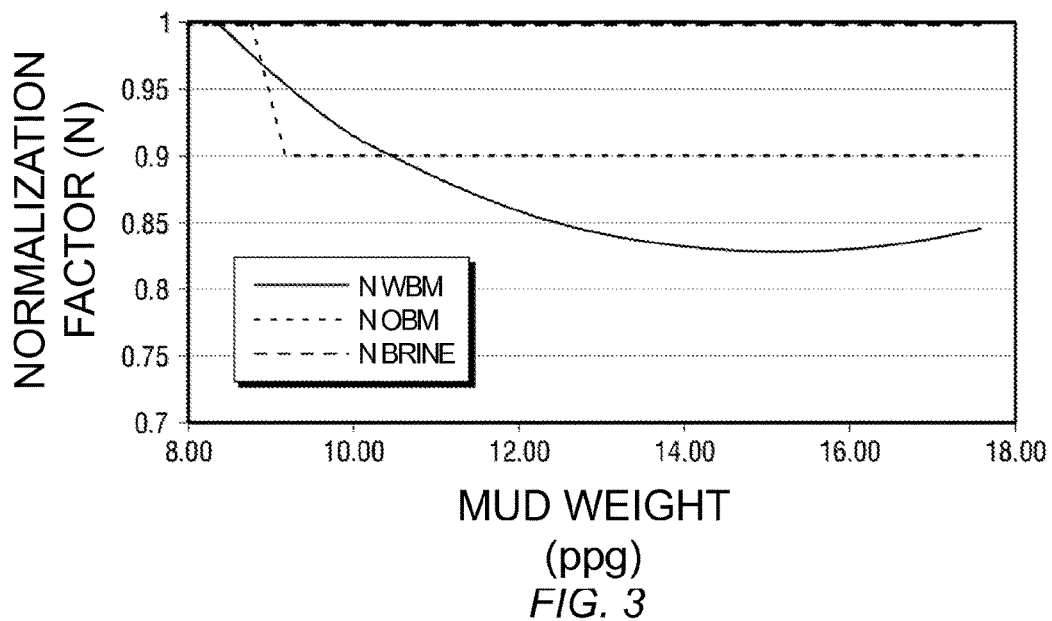
FIG. 3 is a graph depicting one or more aspects of the present disclosure.

FIG. 3 is a graph depicting examples of theoretical normalization factors $N_{theoretical}$ relative to mud weight (in pounds per gallon) based on whether the drilling fluid is water-based mud (WBM), oil-based mud (OBM), or brine. These may be semi-empirical factors based on models and laboratory tests, although others are also within the scope of the present disclosure.

Figure 4:
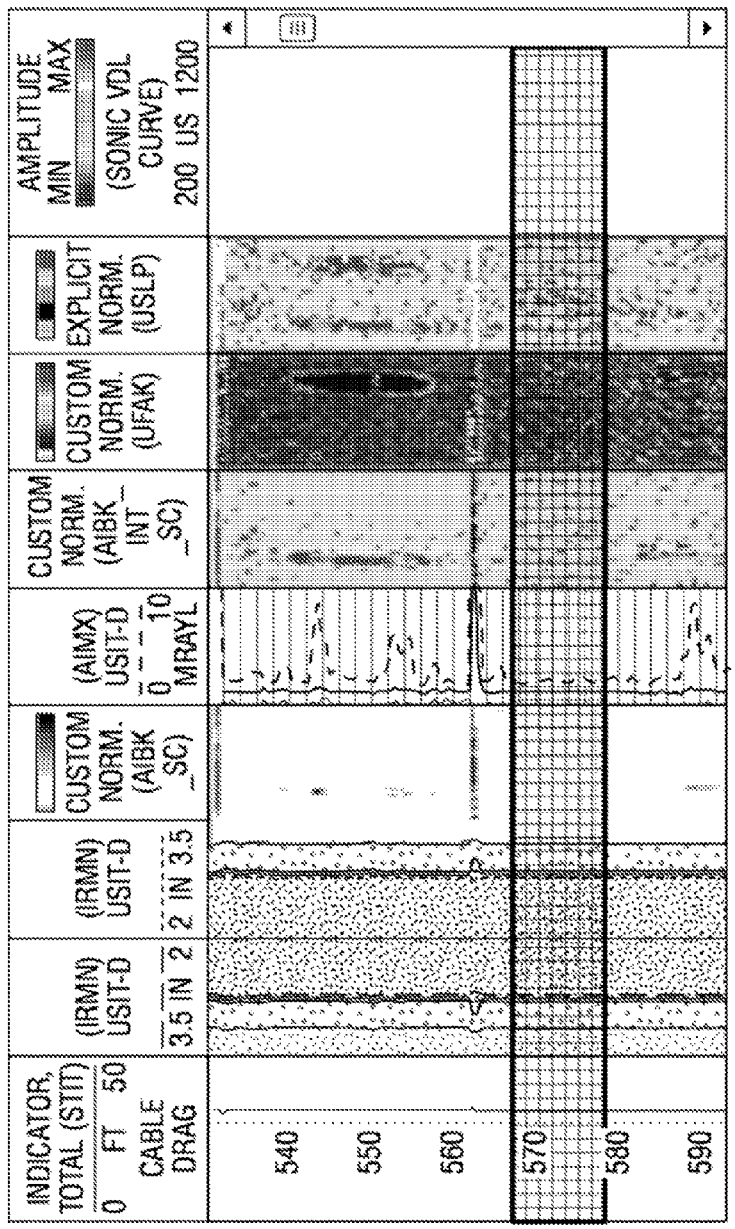
FIG. 4 is a screen capture depicting one or more aspects of the present disclosure.

The free-pipe normalization may iteratively run the processing associated with operation of the downhole tool 105 in a selected known liquid or gas zone to, for example, determine the ZMUD in the free-pipe zone ($ZMUD_{FPZ}$) that makes the median impedance of the cement 30 within the free-pipe zone equal to an expected annulus impedance. The depth zone may be selected on a graphical interface, such as shown in FIG. 4, perhaps by clicking and dragging lines, among other methods within the scope of the present disclosure.

The free-pipe normalization may also be performed in a gas or dry micro-annulus zone, in which case the expected annulus impedance may be set close to about 0.1 MRayl. Moreover, because the calculation utilizes median values over the FP zone, patches of cement may be tolerated within the FP zone, such that the FP zone may not be 100% FP.

The free-pipe normalization factor $N_{free-pipe}$ may be determined as set forth below in Equation (5):

$$N_{free-pipe} = ZMUD_{FPZ} * DEN/FSLO \qquad (5)$$

where DEN is the mud density (g/cm$^3$) and FSLO is the selected mud slowness (s/km) in the free-pipe zone.

The inversion normalization of ZMUD may be utilized if the downhole tool 105 is operable to obtain both pulse-echo and FA measurements. The inversion normalization of ZMUD may determine the ZMUD that makes the impedance of the cement 30 obtained via pulse-echo measurements agree with impedance values calculated from the FA. The impedance of the cement 30 may be low (e.g., less than about 3.5 MRayl). An inversion confidence indicator obtained for QC may show the percentage of "liquid" points that are different from the percentage of points used in the inversion.

Figure 5:
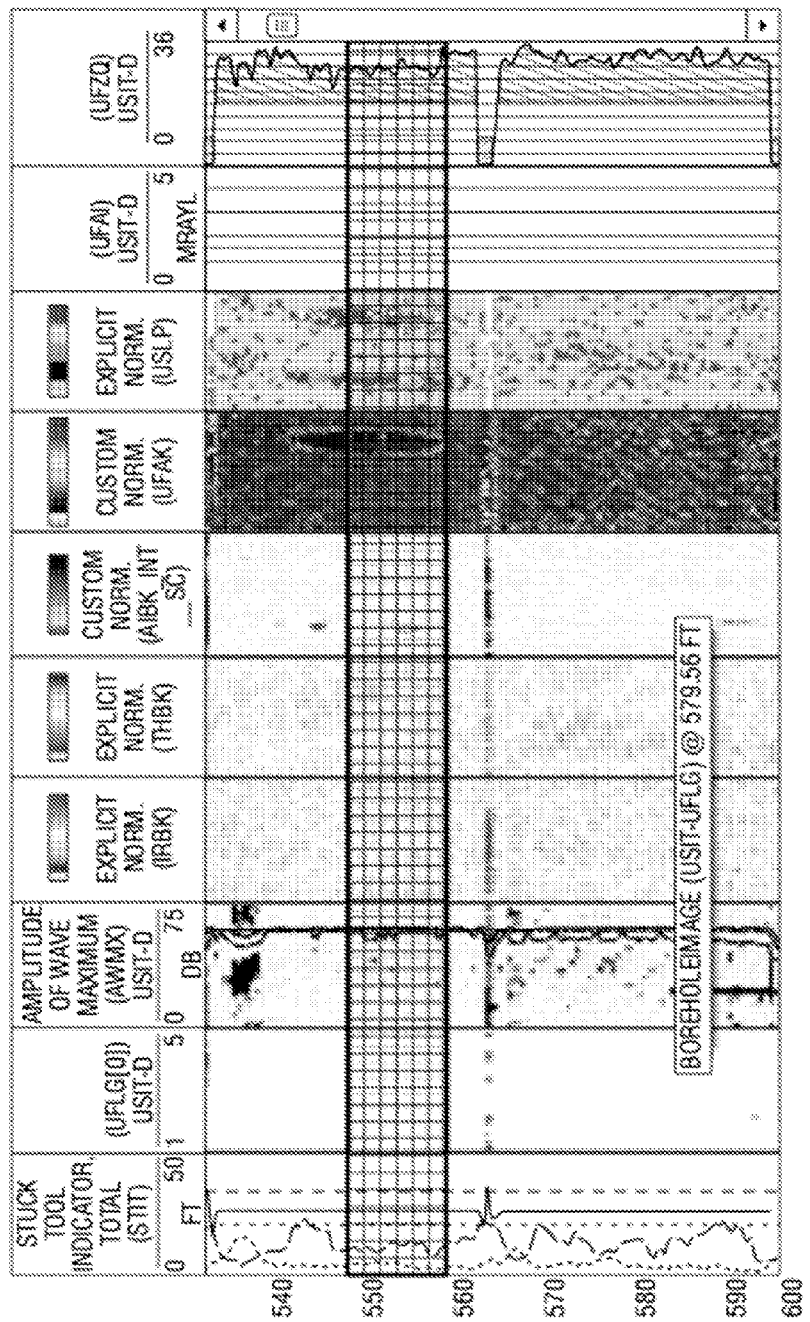
FIG. 5 is a screen capture depicting one or more aspects of the present disclosure.

The inversion normalization of ZMUD may calculate the median inverted ZMUD from the inversion over a zone selected on a graphical interface, as shown in FIG. 5, such as by clicking and dragging lines, among other methods within the scope of the present disclosure. The zone may be selected to have a high percentage of low cement impedance (e.g., less than about 3.5 MRayl), such as to have a sufficient number of suitable points.

The inversion normalization factor $N_{inversion}$ may be determined utilizing Equation (6) set forth below:

$$N_{inversion} = ZMUD_{INV\_ZONE}/(DEN/FSLO) \qquad (6)$$

where $ZMUD_{INV\_ZONE}$ is the median inverted mud impedance, DEN is the mud density (g/cm$^3$), and FSLO is the selected mud slowness (s/km) in the zone. The FSLO selected for utilization in Equation (6) may be the "automatic" value.

Figure 6:
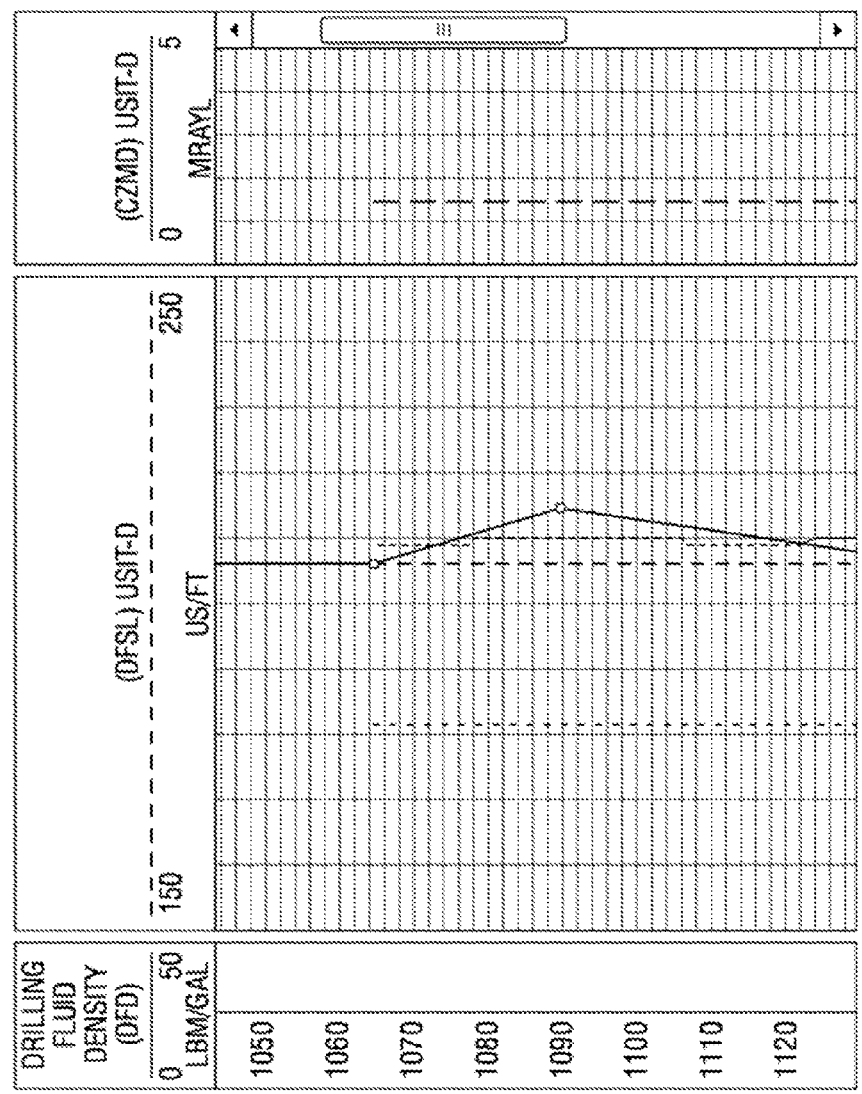
FIG. 6 is a screen capture depicting one or more aspects of the present disclosure.
Figure 7:
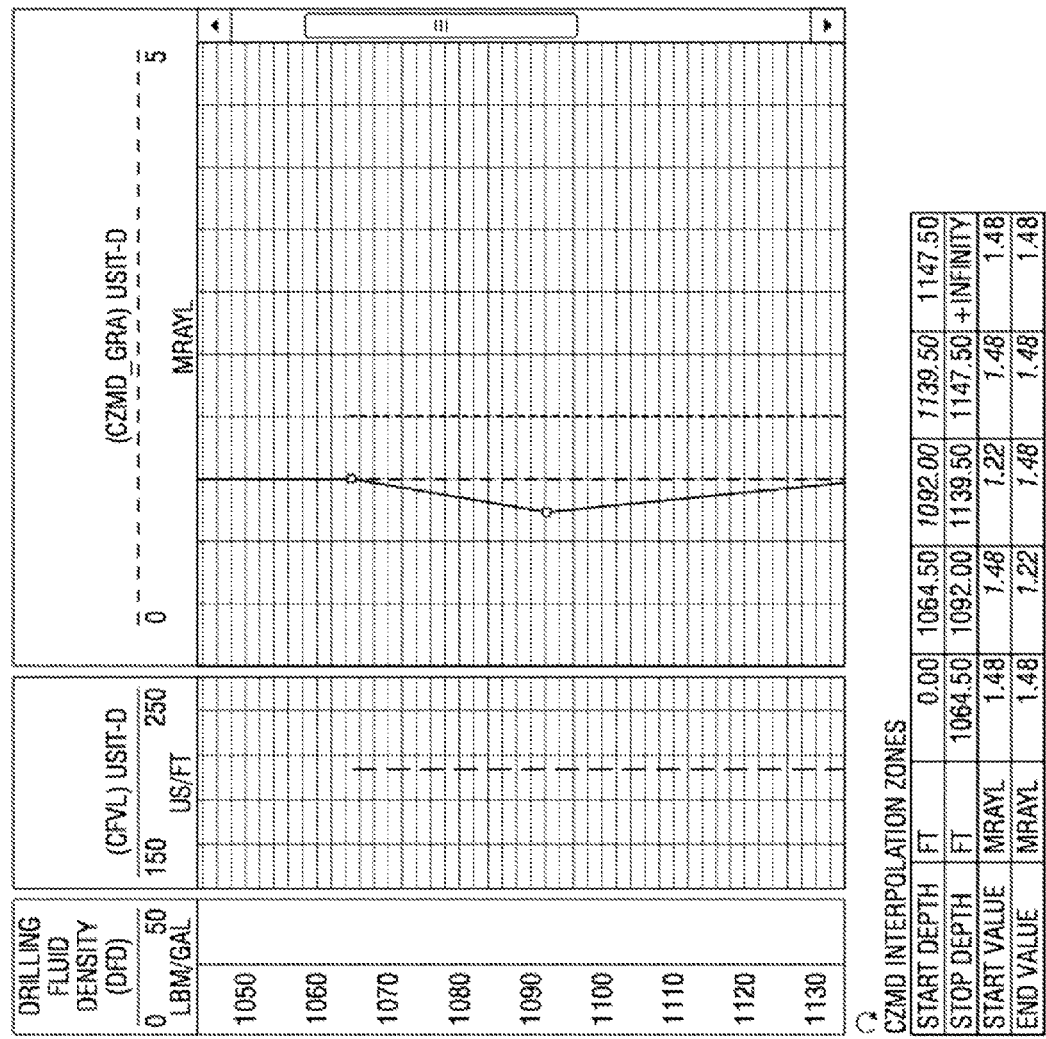
FIG. 7 is a screen capture depicting one or more aspects of the present disclosure.

FIGS. 6 and 7 depict examples of graphical interfaces for FSLO and ZMUD according to one or more aspects of the present disclosure. These and similar graphical interfaces may allow comparison of the various fluid parameter options, plotted against depth, and/or may allow curve creation by clicking on points that may afterwards be dragged to new positions.

Figure 8:
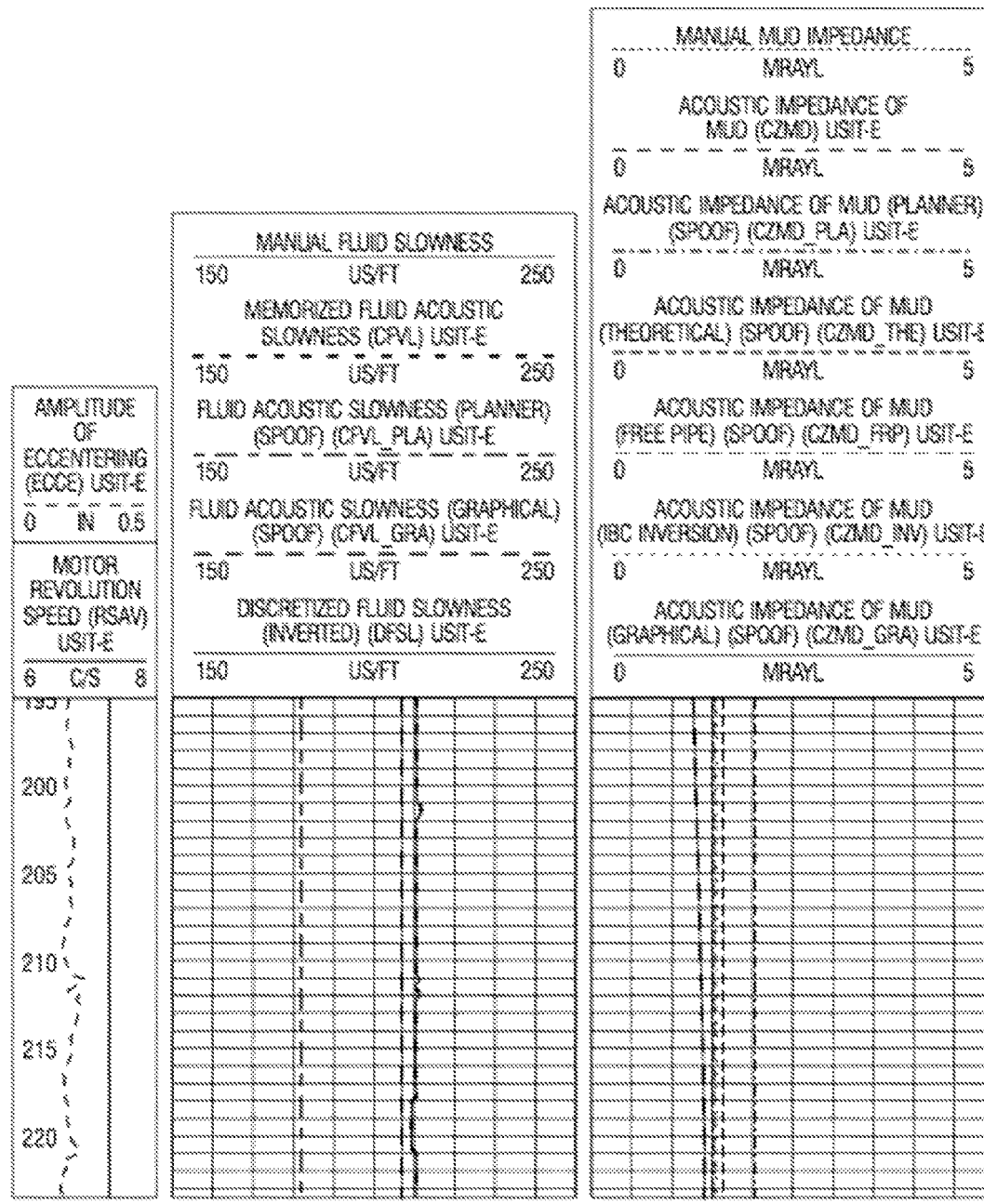
FIG. 8 is a screen capture depicting one or more aspects of the present disclosure.

FIG. 8 depicts each of the above-described estimated and/or measured FSLO and ZMUD curves presented in a QC presentation, such as for traceability purposes. One or more tabular summaries may also or instead be presented in or with the QC presentation, such as to ensure traceability of the processing parameters. Several non-limiting examples are set forth below in Tables 1-3.

TABLE 1

Example Summary Table (Manual FSLO, Manual ZMUD)

| Run Name | Pass Name | Start Depth (ft) | Stop Depth (ft) |
|---|---|---|---|
| Run 1 | Log[2]:Up | 1148.32 | 1065.14 |

Selected FSLO Method: Manual

| Start Depth (ft) | Stop Depth (ft) | Start Value (microseconds/ft) | End Value (microseconds/ft) |
|---|---|---|---|
| 0 | | 206.00 | 206.00 |

Selected ZMUD Method: Manual

| Start Depth (ft) | Stop Depth (ft) | Start Value (MRayl) | End Value (MRayl) |
|---|---|---|---|
| 0 | | 1.48 | 1.48 |

TABLE 2

Example Summary Table (Graphical FSLO, Theoretical ZMUD)

| Run Name | Pass Name | Start Depth (ft) | Stop Depth (ft) |
|---|---|---|---|
| Run 1 | Log[2]:Up | 1148.32 | 1065.14 |

Selected FSLO Method: Graphical

| Start Depth (ft) | Stop Depth (ft) | Start Value (microseconds/ft) | End Value (microseconds/ft) |
|---|---|---|---|
| 0 | 1064.50 | 206.00 | 206.00 |
| 1064.50 | 1089.78 | 206.00 | 214.57 |
| 1089.78 | 1139.50 | 214.57 | 206.00 |
| 1139.50 | 1147.50 | 206.00 | 206.00 |
| 1147.50 | | 206.00 | 206.00 |

Selected ZMUD Method: Theoretical $N_{theoretical}$ = 0.92
Mud Density = 1.20 g/cm³ (10.00 lbm/gal)

| Start Depth (ft) | Stop Depth (ft) | Start Value (MRayl) | End Value (MRayl) |
|---|---|---|---|

TABLE 3

Example Summary Table (Automatic FSLO, Inversion Normalized ZMUD)

| Run Name | Pass Name | Start Depth (ft) | Stop Depth (ft) |
|---|---|---|---|
| Run 1 | Log[2]:Up | 1147.97 | 1072.85 |

Selected FSLO Method: Automatic

| Start Depth (ft) | Stop Depth (ft) | Start Value (microseconds/ft) | End Value (microseconds/ft) |
|---|---|---|---|

TABLE 3-continued

Example Summary Table (Automatic FSLO, Inversion Normalized ZMUD)

Selected ZMUD Method: Inversion Normalized

Inversion normalization zone: 166.74 m (547.06 ft) to 170.05 m (557.90 ft)
$N_{inversion}$ = 0.86
Mud Density = 1.20 g/cm³ (10.00 lbm/gal)
ZMUD median computed in inversion normalization interval: 1.52 MRayl

| Start Depth (ft) | Stop Depth (ft) | Start Value (MRayl) | End Value (MRayl) |
|---|---|---|---|

Figure 9:
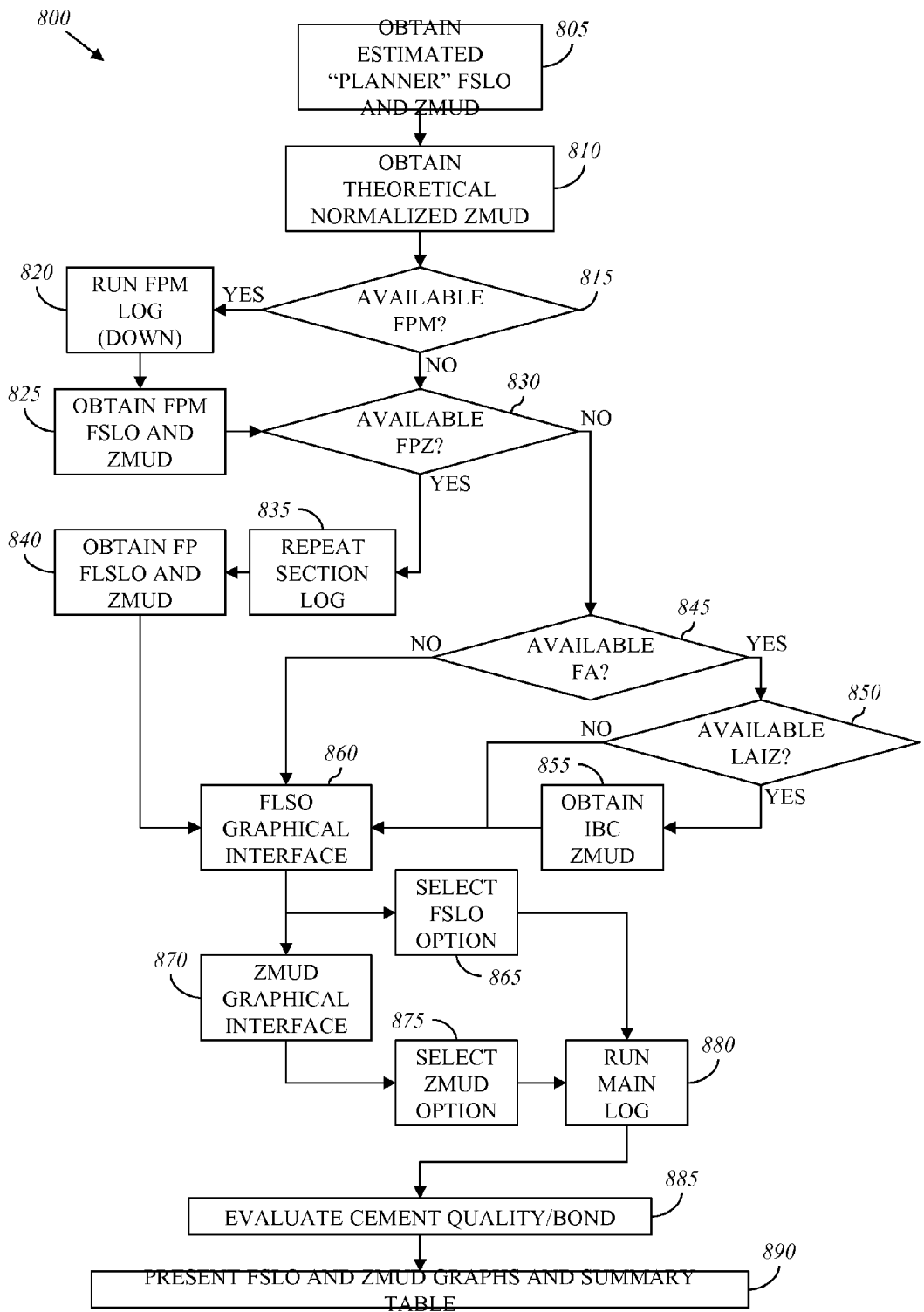
FIG. 9 is a flow-chart diagram of at least a portion of a method according to one or more aspects of the present disclosure.

FIG. 9 is a flow-chart diagram of at least a portion of a method (800) according to one or more aspects of the present disclosure. The method (800) implements one or more aspects described above, and may be performed by operation of the downhole tool 105 and the surface equipment 125 shown in FIG. 1. Accordingly, the following description refers to FIGS. 1 and 9, collectively.

The method (800) includes operating the surface equipment 125 of the cement analysis system (CAS) 100 to estimate (805) a drilling fluid slowness (FSLO) and a drilling fluid acoustic impedance (ZMUD) based on a type and predetermined density of the drilling fluid. Such estimates (805) may be performed via one or more tool planners associated with the downhole tool 105 and/or surface equipment 125, as described above. The method (800) may also include normalizing (810) ZMUD by obtaining a theoretical normalization factor, as described above.

If the downhole tool 105 includes apparatus for obtaining FPM measurements (the determination of which being represented in FIG. 9 by decision 815), the downhole tool 105 is then conveyed (820) within the wellbore 10 while operating the CAS 100 to obtain (825) first log data that includes another FSLO and ZMUD, each measured with respect to depth in the wellbore 10. Such "FPM log" may be obtained (825) as the downhole tool 105 is conveyed (820) in a direction that is generally down or deeper into the wellbore 10.

The downhole tool 105 may then be conveyed to repeat (835) a short log. For example, if a free-pipe (FP) zone of the wellbore 10 is available (the determination of which being represented in FIG. 9 by decision 830), the CAS 100 is then operated to obtain (840) a FP FSLO and/or ZMUD. For example, such FSLO may be based on a thickness and external diameter of the casing 20 and a transit time for energy emitted by the downhole tool transmitter 130 to travel to and from the casing 20.

In the absence of a free pipe zone, and if a flexural attenuation (FA) measurement is available (the determination of which being represented in FIG. 9 by decision 845), and there exists a suitable low annulus impedance (<3.5 MRayl) zone (the determination of which being represented in FIG. 9 by decision 850), then a combined inversion of the pulse-echo and FA measurements is performed (855) to obtain another "IBC" estimate of ZMUD.

The CAS 100 is then operated to generate (860) an FSLO graphical interface (such as shown in FIG. 6) based on available estimates of FLSO. One FLSO estimate is chosen (865). The CAS 100 is then operated to generate (870) a ZMUD graphical interface (such as shown in FIG. 7) based on the available estimates of ZMUD. One ZMUD estimate is chosen (875).

The downhole tool 105 is then conveyed within the wellbore 10 while operating the CAS 100 to obtain (880) the main log data utilizing at least one parameter based on at least one of the FSLO and ZMUD graphical interfaces. Such "main log" may be obtained (880) as the downhole tool 105 is conveyed in a direction that is generally up the wellbore 10, or opposite the direction of conveyance during the FPM log (820).

Operating the CAS 100 to obtain (820) the FPM log data and to obtain (880) the main log data may include obtaining pulse-echo measurements and flexural attenuation measurements utilizing the downhole tool 105. The method (800) may also include utilizing the main log to evaluate (885) the cement quality and bond, as well as to present (890) the generated FSLO and ZMUD graphs and summary tables, as described above.

Figure 10:
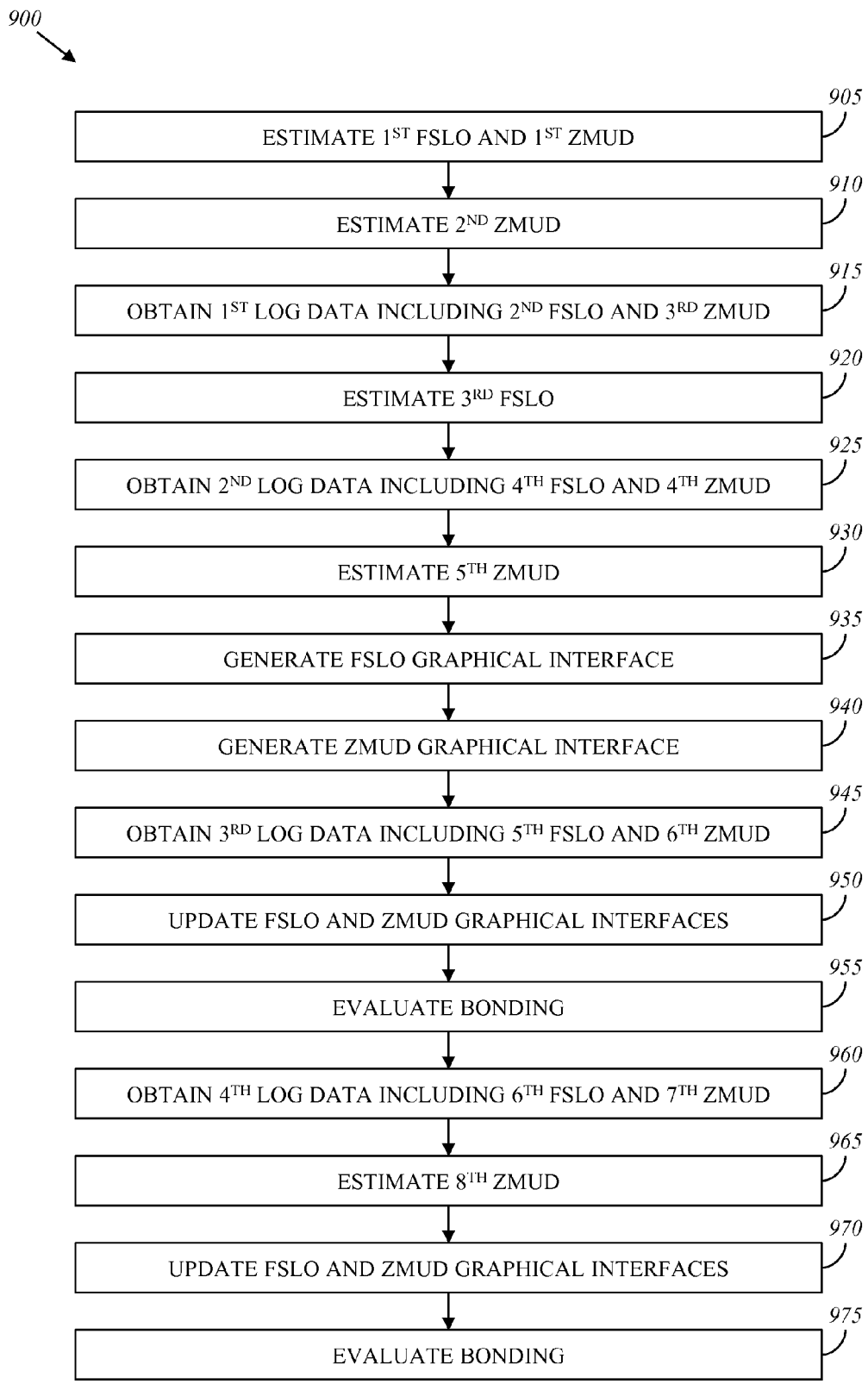
FIG. 10 is a flow-chart diagram of at least a portion of a method according to one or more aspects of the present disclosure.

FIG. 10 is a flow-chart diagram of at least a portion of a method (900) according to one or more aspects of the present disclosure. The method (900) may implement one or more aspects described above, and may be performed by operation of the downhole tool 105 and the surface equipment 125 shown in FIG. 1. Accordingly, the following description refers to FIGS. 1 and 10, collectively.

The method (900) includes operating the surface equipment 125 of the CAS 100 to estimate (905) a first drilling fluid slowness (FSLO) and a first drilling fluid acoustic impedance (ZMUD), such as may be based on a type and predetermined density of the drilling fluid. The CAS 100 may then be operated to estimate (910) a second ZMUD based on the first FSLO, the type, and the predetermined density.

The downhole tool 105 may then be conveyed within the wellbore 10 while operating the CAS 100 to obtain (915) first log data that includes a second FSLO and a third ZMUD each measured with respect to depth in the wellbore 10. The CAS 100 is then operated to estimate (920) a third FSLO based on a thickness and external diameter of the casing 20 and a transit time for energy emitted by the downhole tool transmitter 130 to travel to and from the casing 20.

The downhole tool 105 may then be conveyed in a free-pipe (FP) zone of the wellbore 10 while operating the CAS 100 to obtain (925) second log data that includes a fourth FSLO and a fourth ZMUD each measured with respect to depth in the FP zone. The CAS 100 may then be operated to estimate (930) a fifth ZMUD based on the fourth ZMUD, the predetermined density of the drilling fluid, the first FSLO, and an expected impedance in the annulus/ cement 30.

The CAS 100 may then be operated to generate (935) an FSLO graphical interface (such as shown in FIG. 6) based on the first FSLO, the second FSLO, the third FSLO, and the fourth FSLO. The CAS 100 may then be operated to generate (940) a ZMUD graphical interface (such as shown in FIG. 7) based on the first ZMUD, the second ZMUD, the third ZMUD, the fourth ZMUD, and the fifth ZMUD.

The downhole tool 105 may then be conveyed within the wellbore 10 while operating the CAS 100 to obtain (945) third log data utilizing at least one parameter based on the ZMUD graphical interface, wherein the third log data includes a fifth FSLO and a sixth ZMUD measured with respect to depth in the wellbore 10. The CAS 100 may then be operated to update (950) the FSLO and ZMUD graphical interfaces based on the fifth FSLO and the sixth ZMUD, respectively.

The method (900) may also include evaluating (955) bonding between the casing 20 and the cement 30 utilizing, for example, the ZMUD graphical interface updated with the sixth ZMUD.

The method (900) may also include conveying the downhole tool in the FP zone again while operating the CAS to obtain (960) fourth log data that includes a sixth FSLO and a seventh ZMUD each with respect to depth in the FP zone. An eighth ZMUD may be estimated (965) based on the seventh ZMUD, the predetermined density of the drilling fluid, the first FSLO, and the expected impedance in the annulus/cement 30. The FSLO and ZMUD graphical interfaces may then be updated (970) based on the sixth FSLO and the eighth ZMUD, respectively. The method (900) may also include evaluating (975) bonding between the casing 20 and the cement 30 utilizing the ZMUD graphical interface updated with the sixth ZMUD and the eighth ZMUD.

Conveying the downhole tool 105 within the wellbore 10 while operating the CAS 100 to obtain (915) the first log data may include conveying the downhole tool in a first direction relative to the wellbore, whereas conveying the downhole tool 105 within the wellbore 10 while operating the CAS 100 to obtain (945) the third log data may include conveying the downhole tool 105 in a second direction relative to the wellbore 10. The first direction may be substantially opposite the second direction.

Operating the CAS 100 to obtain (915) the first log data, to obtain (925) the second log data, and to obtain (945) the third log data may include obtaining pulse-echo measurements via operation of the downhole tool 105.

Figure 11:
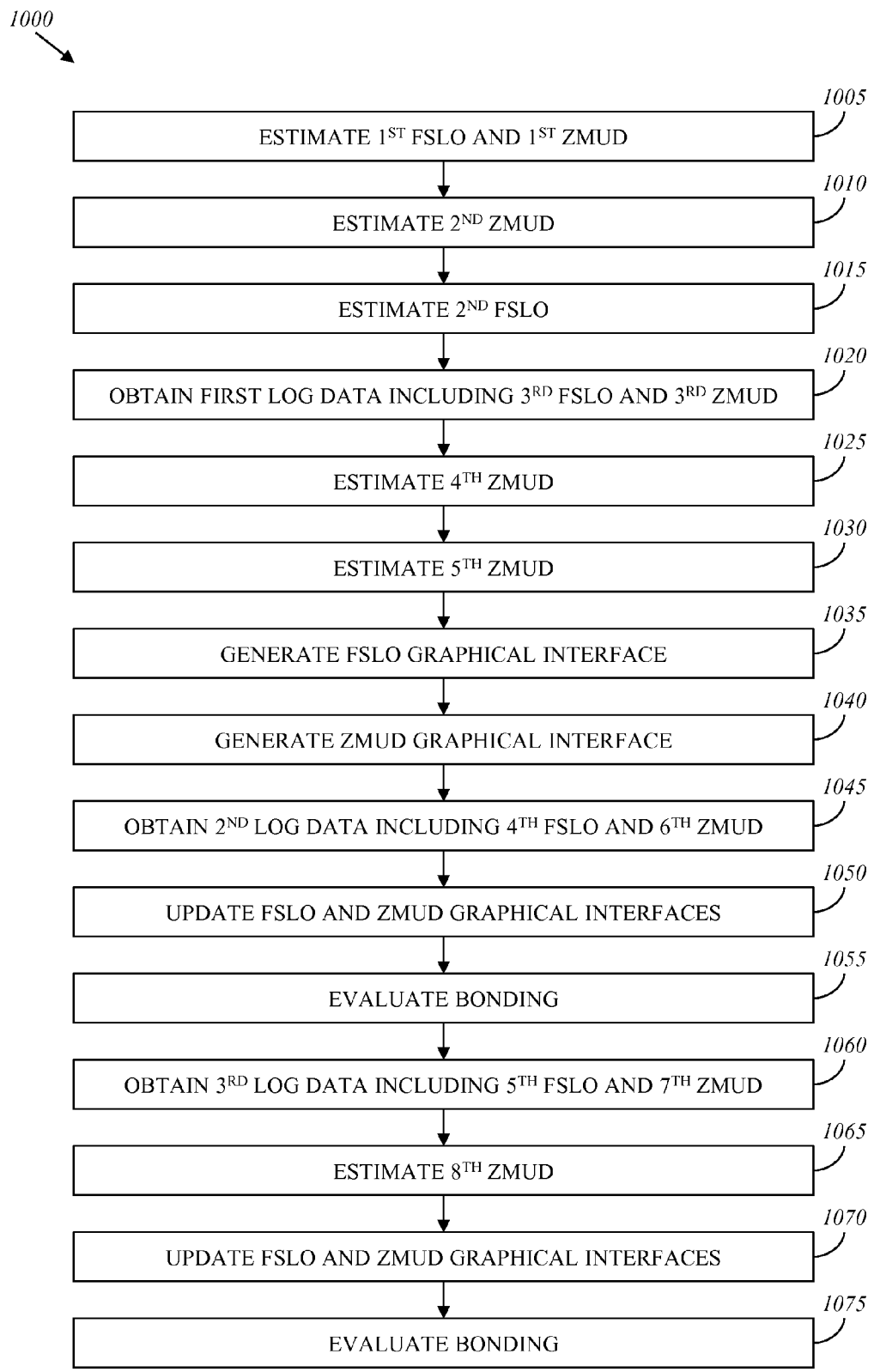
FIG. 11 is a flow-chart diagram of at least a portion of a method according to one or more aspects of the present disclosure.

FIG. 11 is a flow-chart diagram of at least a portion of a method (1000) according to one or more aspects of the present disclosure. The method (1000) may implement one or more aspects described above, and may be performed by operation of the downhole tool 105 and the surface equipment 125 shown in FIG. 1. Accordingly, the following description refers to FIGS. 1 and 11, collectively.

The method (1000) includes operating the surface equipment 125 of the CAS 100 to estimate (1005) a first drilling fluid slowness (FSLO) and a first drilling fluid acoustic impedance (ZMUD) based on a type and predetermined density of the drilling fluid in the wellbore 10. The CAS 100 may then be operated to estimate (1010) a second ZMUD based on the first FSLO, the type, and the predetermined density. The CAS 100 may then be operated to estimate (1015) a second FSLO, perhaps based on a thickness and external diameter of the casing and a transit time for energy emitted by the transmitter 130 of the downhole tool 105 to travel to and from the casing 20.

The downhole tool 105 may then be conveyed within a free-pipe (FP) zone of the wellbore 10 while operating the CAS 100 to obtain (1020) first log data that includes a third FSLO and a third ZMUD each measured with respect to depth in the FP zone. The CAS 100 may then be operated to estimate (1025) a fourth ZMUD based on the third ZMUD, the predetermined density, the first FSLO, and an expected impedance in the annulus/cement 30. The CAS 100 may then be operated to estimate (1030) a fifth ZMUD based on: a median of one of the third ZMUD and the fourth ZMUD in the FP zone; one of the first FSLO, the second FSLO, and the third FSLO; and the predetermined density.

The CAS 100 may then be operated to generate (1035) an FSLO graphical interface (such as shown in FIG. 6) based on the first FSLO, the second FSLO, and the third FSLO, and to generate (1040) a ZMUD graphical interface (such as shown in FIG. 7) based on the first ZMUD, the second ZMUD, the third ZMUD, the fourth ZMUD, and the fifth ZMUD. The downhole tool 105 may then be conveyed within the wellbore 10 while operating the CAS 100 to obtain (1045) second log data utilizing at least one parameter based on the ZMUD graphical interface, wherein the second log data includes a fourth FSLO and a sixth ZMUD measured with respect to depth in the wellbore 10. The CAS

100 may then be operated to update (1050) the FSLO and ZMUD graphical interfaces based on the fourth FSLO and the sixth ZMUD, respectively. The method (1000) may also include evaluating (1055) the cement 30 and/or bonding between the casing 20 and the cement 30, perhaps by utilizing at least one of the updated (1050) FSLO and ZMUD graphical interfaces.

The method (1000) may also include conveying the downhole tool 105 in the FP zone again while operating the CAS 100 to obtain (1060) third log data that includes a fifth FSLO and a seventh ZMUD each with respect to depth in the FP zone. The CAS 100 may then be operated to estimate (1065) an eighth ZMUD based on the seventh ZMUD, the predetermined density, the first FSLO, and the expected impedance in the annulus/cement 30. The CAS 100 may then be operated to update (1070) the FSLO and ZMUD graphical interfaces based on the fifth FSLO and the eighth ZMUD, respectively. The method (1000) may also include evaluating (1075) the cement 20 and/or the bonding between the casing 20 and the cement 30 utilizing the ZMUD graphical interface updated with the sixth ZMUD and the eighth ZMUD.

Operating the CAS 100 to obtain (1020) the first log data and to obtain (1045) the second log data may include obtaining pulse-echo measurements and flexural attenuation measurements utilizing the downhole tool 105.

Figure 12:
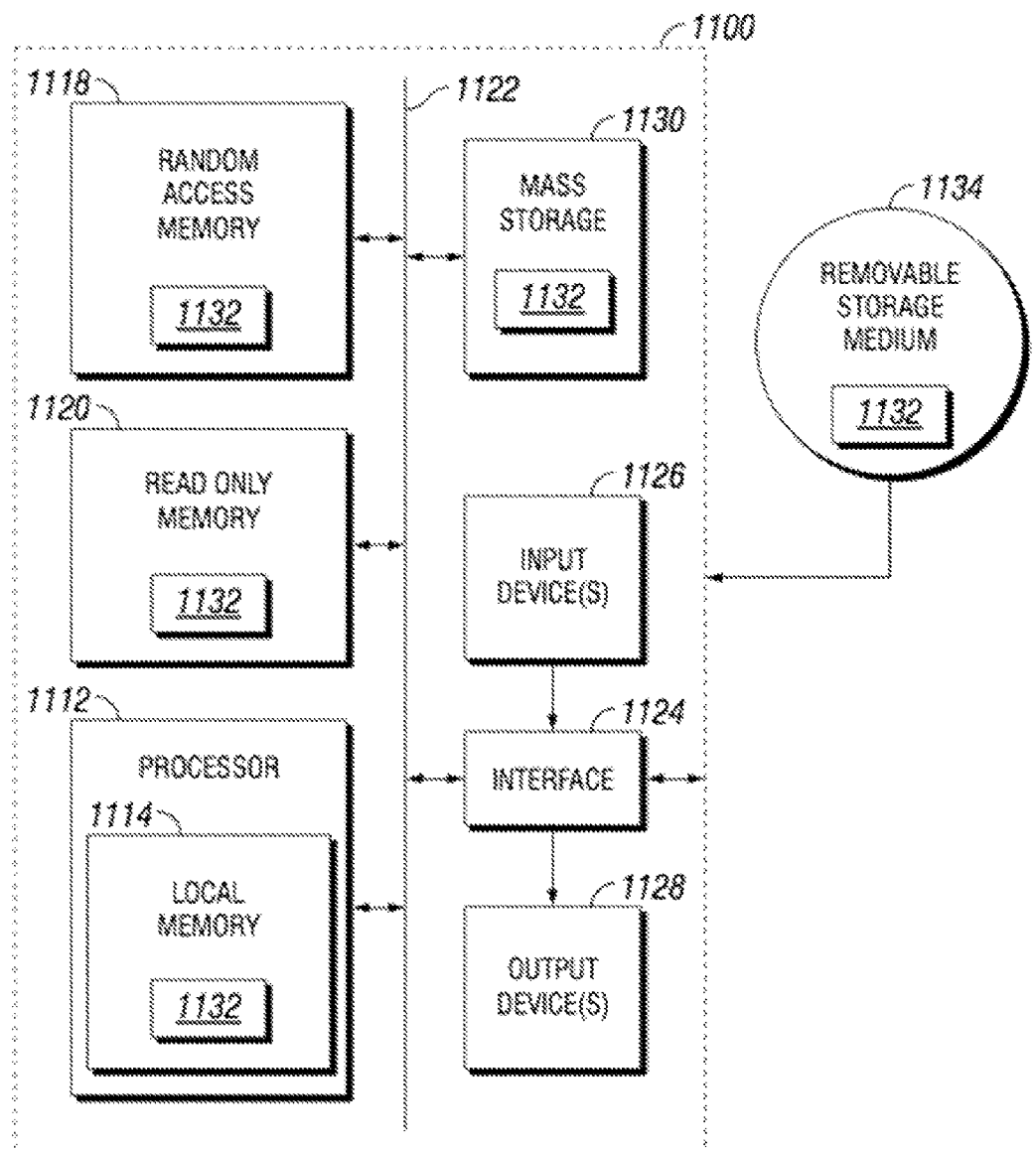
FIG. 12 is a schematic view of at least a portion of apparatus according to one or more aspects of the present disclosure.

FIG. 12 is a block diagram of an example processing system 1100 that may execute example machine-readable instructions used to implement one or more of the methods and/or processes described herein, and/or to implement the example downhole tools described herein. The processing system 1100 may be at least partially implemented in one or more of the downhole tool 105 and the surface equipment 125 shown in FIG. 1.

The processing system 1100 may be or comprise, for example, one or more processors, one or more controllers, one or more special-purpose computing devices, one or more servers, one or more personal computers, one or more personal digital assistant (PDA) devices, one or more smartphones, one or more internet appliances, and/or any other type(s) of computing device(s).

The system 1100 comprises a processor 1112 such as, for example, a general-purpose programmable processor. The processor 1112 includes a local memory 1114, and executes coded instructions 1132 present in the local memory 1114 and/or in another memory device. The processor 1112 may execute, among other things, machine-readable instructions to implement the methods and/or processes described herein. The processor 1112 may be, comprise or be implemented by any type of processing unit, such as one or more INTEL microprocessors, one or more microcontrollers from the ARM and/or PICO families of microcontrollers, one or more embedded soft/hard processors in one or more FPGAs, etc. Of course, other processors from other families are also appropriate.

The processor 1112 is in communication with a main memory including a volatile (e.g., random access) memory 1118 and a non-volatile (e.g., read only) memory 1120 via a bus 1122. The volatile memory 1118 may be, comprise or be implemented by static random access memory (SRAM), synchronous dynamic random access memory (SDRAM), dynamic random access memory (DRAM), RAMBUS dynamic random access memory (RDRAM) and/or any other type of random access memory device. The non-volatile memory 1120 may be, comprise or be implemented by flash memory and/or any other desired type of memory device. One or more memory controllers (not shown) may control access to the main memory 1118 and/or 1120.

The processing system 1100 also includes an interface circuit 1124. The interface circuit 1124 may be, comprise or be implemented by any type of interface standard, such as an Ethernet interface, a universal serial bus (USB) and/or a third generation input/output (3GIO) interface, among others.

One or more input devices 1126 are connected to the interface circuit 1124. The input device(s) 1126 permit a user to enter data and commands into the processor 1112. The input device(s) may be, comprise or be implemented by, for example, a keyboard, a mouse, a touchscreen, a track-pad, a trackball, an isopoint and/or a voice recognition system, among others.

One or more output devices 1128 are also connected to the interface circuit 1124. The output devices 1128 may be, comprise or be implemented by, for example, display devices (e.g., a liquid crystal display or cathode ray tube display (CRT), among others), printers and/or speakers, among others. Thus, the interface circuit 1124 may also comprise a graphics driver card.

The interface circuit 1124 also includes a communication device such as a modem or network interface card to facilitate exchange of data with external computers via a network (e.g., Ethernet connection, digital subscriber line (DSL), telephone line, coaxial cable, cellular telephone system, satellite, etc.).

The processing system 1100 also includes one or more mass storage devices 1130 for storing machine-readable instructions and data. Examples of such mass storage devices 1130 include floppy disk drives, hard drive disks, compact disk drives and digital versatile disk (DVD) drives, among others.

The coded instructions 1132 may be stored in the mass storage device 1130, the volatile memory 1118, the non-volatile memory 1120, the local memory 1114 and/or on a removable storage medium, such as a CD or DVD 1134.

As an alternative to implementing the methods and/or apparatus described herein in a system such as the processing system of FIG. 12, the methods and or apparatus described herein may be embedded in a structure such as a processor and/or an ASIC (application specific integrated circuit).

The present disclosure also introduces a method comprising: operating surface equipment of a cement analysis system (CAS) to estimate a first drilling fluid slowness (FSLO) and a first drilling fluid acoustic impedance (ZMUD) based on a type and density of the drilling fluid, wherein the drilling fluid is in a wellbore extending from a wellsite surface, a steel casing is secured within the wellbore by cement in an annulus between an external diameter of the casing and the wellbore, and the surface equipment is disposed at the wellsite surface and comprises a processor; conveying a downhole tool of the CAS within the wellbore; operating the CAS to estimate a second FSLO based on a thickness of the casing, the external diameter, and a transit time for energy emitted by the downhole tool to travel to and from the casing; operating the CAS to generate an FSLO graphical interface based on the first FSLO and the second FSLO; operating the CAS to estimate a second ZMUD based on the type and density of the drilling fluid and a selected one of the first FSLO and the second FSLO, wherein the selected one of the first FSLO and the second FSLO is selected utilizing the FSLO graphical interface; operating the CAS to generate a ZMUD graphical interface based on the first ZMUD and the second ZMUD; and conveying the downhole tool within the wellbore while operating the CAS to obtain log data utilizing at least one parameter selected utilizing the ZMUD graphical interface, wherein the log data includes a final ZMUD measured with respect to depth in the wellbore.

The type and density of the drilling fluid may be predetermined.

The log data may be first log data and the method may further comprise conveying the downhole tool within the wellbore while operating the CAS to obtain second log data that includes a third FSLO and a third ZMUD each measured with respect to depth in the wellbore, wherein the FSLO and ZMUD graphical interfaces may be generated further based on the third FSLO and the third ZMUD, respectively. The first log data may be obtained while conveying the downhole tool in a first direction, and the second log data may be obtained while conveying the downhole tool in a second direction that is substantially opposite the first direction.

The method may further comprise operating the CAS to estimate a third ZMUD based on the density, an expected impedance in the annulus, a selected one of the first FSLO and the second FSLO, and a selected one of the first ZMUD and the second ZMUD, and wherein the ZMUD graphical interface is generated further based on the third ZMUD.

The log data may be first log data and the method may further comprise conveying the downhole tool in a free-pipe (FP) zone of the wellbore while operating the CAS to obtain second log data that includes a third FSLO and a third ZMUD each measured with respect to depth in the FP zone, and the FSLO and ZMUD graphical interfaces may be generated further based on the third FSLO and the third ZMUD, respectively. The method may further comprise conveying the downhole tool in the FP zone again while operating the CAS to obtain third log data that includes a fourth FSLO and a fourth ZMUD each measured with respect to depth in the FP zone, and the FSLO and ZMUD graphical interfaces may be generated further based on the fourth FSLO and the fourth ZMUD, respectively.

Operating the CAS to obtain the log data may comprise operating the downhole tool to obtain pulse-echo measurements, or operating the CAS to obtain the log data may comprise operating the downhole tool to obtain pulse-echo measurements and flexural attenuation measurements.

The present disclosure also introduces a method comprising: operating surface equipment of a cement analysis system (CAS) to estimate a first drilling fluid slowness (FSLO) and a first drilling fluid acoustic impedance (ZMUD) based on a predetermined type and a predetermined density of the drilling fluid, wherein the drilling fluid is in a wellbore extending from a wellsite surface, a steel casing is secured within the wellbore by cement in an annulus between an external diameter of the casing and the wellbore, and the surface equipment is disposed at the wellsite surface and comprises a processor; conveying a downhole tool of the CAS within the wellbore while operating the CAS to obtain first log data that includes a second FSLO and a second ZMUD each measured with respect to depth in the wellbore; operating the CAS to estimate a third FSLO based on a thickness of the casing, the external diameter, and a transit time for energy emitted by the downhole tool to travel to and from the casing; operating the CAS to estimate a third ZMUD based on the predetermined density, an expected impedance in the annulus, a selected one of the first FSLO, the second FSLO, and the third FSLO, and a selected one of the first ZMUD, the second ZMUD, and the third ZMUD; conveying the downhole tool in a free-pipe (FP) zone of the wellbore while operating the CAS to obtain second log data that includes a fourth FSLO and a fourth ZMUD each measured with respect to depth in the FP zone; operating the CAS to generate an FSLO graphical interface based on the first FSLO, the second FSLO, the third FSLO, and the fourth FSLO; operating the CAS to estimate a fifth ZMUD based on the predetermined type and predetermined density of the drilling fluid and a selected one of the first FSLO, the second FSLO, the third FSLO, and the fourth FSLO, wherein the selected one of the first FSLO, the second FSLO, the third FSLO, and the fourth FSLO is selected utilizing the FSLO graphical interface; operating the CAS to generate a ZMUD graphical interface based on the first ZMUD, the second ZMUD, the third ZMUD, the fourth ZMUD, and the fifth ZMUD; and conveying the downhole tool within the wellbore while operating the CAS to obtain third log data utilizing at least one parameter selected utilizing the ZMUD graphical interface, wherein the third log data includes a final ZMUD measured with respect to depth in the wellbore.

The first log data may be obtained while conveying the downhole tool in a first direction, and the third log data may be obtained while conveying the downhole tool in a second direction that is substantially opposite the first direction. Operating the CAS to obtain the first log data and the third log data may comprise operating the downhole tool to obtain pulse-echo measurements, or to obtain pulse-echo measurements and flexural attenuation measurements. The method may further comprise conveying the downhole tool in the FP zone again while operating the CAS to obtain fourth log data that includes a fifth FSLO and a sixth ZMUD each measured with respect to depth in the FP zone, and the FSLO and ZMUD graphical interfaces may be generated further based on the fifth FSLO and the sixth ZMUD, respectively.

The present disclosure also introduces an apparatus comprising: surface equipment disposed at a wellsite surface and comprising a processor, wherein a wellbore extending from the wellsite surface comprises a steel casing secured within the wellbore by cement in an annulus between an external diameter of the casing and the wellbore, wherein an amount of drilling fluid fills at least a portion of the casing, and wherein the surface equipment is operable to: estimate a first drilling fluid slowness (FSLO) and a first drilling fluid acoustic impedance (ZMUD) based on a type and density of the drilling fluid; estimate a second FSLO based on a thickness of the casing, the external diameter, and a transit time for energy emitted by the downhole tool to travel to and from the casing; generate an FSLO graphical interface based on the first FSLO and the second FSLO; estimate a second ZMUD based on the type and density of the drilling fluid and a selected one of the first FSLO and the second FSLO, wherein the selected one of the first FSLO and the second FSLO is selected utilizing the FSLO graphical interface; and generate a ZMUD graphical interface based on the first ZMUD and the second ZMUD; and a downhole tool operable for conveyance within the drilling fluid inside the wellbore while obtaining log data utilizing at least one parameter selected utilizing the ZMUD graphical interface, wherein the log data includes a final ZMUD measured with respect to depth in the wellbore.

The log data may include pulse-echo measurements, or pulse-echo measurements and flexural attenuation measurements. The log data may be first log data and the downhole tool may be further operable for conveyance within the drilling fluid inside the wellbore while obtaining second log data that includes a third FSLO and a third ZMUD each measured with respect to depth in the wellbore, and the FSLO and ZMUD graphical interfaces may be generated further based on the third FSLO and the third ZMUD, respectively. The first log data may be obtained while conveying the downhole tool in a first direction, and the second log data may be obtained while conveying the downhole tool in a second direction that is substantially opposite the first direction. The log data may be first log data and the downhole tool may be further operable for conveyance within the drilling fluid inside a free-pipe (FP) zone of the wellbore while obtaining second log data that includes a third FSLO and a third ZMUD each measured with respect to depth in the FP zone, and the FSLO and ZMUD graphical interfaces may be generated further based on the third FSLO and the third ZMUD, respectively.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method, comprising:
    operating surface equipment of a cement analysis system (CAS) to estimate a first drilling fluid slowness (FSLO) and a first drilling fluid acoustic impedance (ZMUD) based on a type and density of the drilling fluid, wherein the drilling fluid is in a wellbore extending from a wellsite surface, a steel casing is secured within the wellbore by cement in an annulus between an external diameter of the casing and the wellbore, and the surface equipment is disposed at the wellsite surface and comprises a processor;
    conveying a downhole tool of the CAS within the wellbore;
    operating the CAS to estimate a second FSLO based on a thickness of the casing, the external diameter, and a transit time for energy emitted by the downhole tool to travel to and from the casing;
    operating the CAS to generate an FSLO graphical interface based on the first FSLO and the second FSLO;
    operating the CAS to estimate a second ZMUD based on the type and density of the drilling fluid and a selected one of the first FSLO and the second FSLO, wherein the selected one of the first FSLO and the second FSLO is selected utilizing the FSLO graphical interface;
    operating the CAS to generate a ZMUD graphical interface based on the first ZMUD and the second ZMUD; and
    conveying the downhole tool within the wellbore while operating the CAS to obtain log data utilizing at least one parameter selected utilizing the ZMUD graphical interface, wherein the log data includes a final ZMUD measured with respect to depth in the wellbore.

2. The method of claim 1 wherein the type and density of the drilling fluid are predetermined.

3. The method of claim 1 wherein the log data is first log data and the method further comprises conveying the downhole tool within the wellbore while operating the CAS to obtain second log data that includes a third FSLO and a third ZMUD each measured with respect to depth in the wellbore, wherein the FSLO and ZMUD graphical interfaces are generated further based on the third FSLO and the third ZMUD, respectively.

4. The method of claim 3 wherein the first log data is obtained while conveying the downhole tool in a first direction, and wherein the second log data is obtained while conveying the downhole tool in a second direction that is substantially opposite the first direction.

5. The method of claim 1 further comprising operating the CAS to estimate a third ZMUD based on the density, an expected impedance in the annulus, a selected one of the first FSLO and the second FSLO, and a selected one of the first ZMUD and the second ZMUD, and wherein the ZMUD graphical interface is generated further based on the third ZMUD.

6. The method of claim 1 wherein the log data is first log data and the method further comprises conveying the downhole tool in a free-pipe (FP) zone of the wellbore while operating the CAS to obtain second log data that includes a third FSLO and a third ZMUD each measured with respect to depth in the FP zone, and wherein the FSLO and ZMUD graphical interfaces are generated further based on the third FSLO and the third ZMUD, respectively.

7. The method of claim 6 further comprising conveying the downhole tool in the FP zone again while operating the CAS to obtain third log data that includes a fourth FSLO and a fourth ZMUD each measured with respect to depth in the FP zone, and wherein the FSLO and ZMUD graphical interfaces are generated further based on the fourth FSLO and the fourth ZMUD, respectively.

8. The method of claim 1 wherein operating the CAS to obtain the log data comprises operating the downhole tool to obtain pulse-echo measurements.

9. The method of claim 1 wherein operating the CAS to obtain the log data comprises operating the downhole tool to obtain pulse-echo measurements and flexural attenuation measurements.

10. A method, comprising:
    operating surface equipment of a cement analysis system (CAS) to estimate a first drilling fluid slowness (FSLO) and a first drilling fluid acoustic impedance (ZMUD) based on a predetermined type and a predetermined density of the drilling fluid, wherein the drilling fluid is in a wellbore extending from a wellsite surface, a steel casing is secured within the wellbore by cement in an annulus between an external diameter of the casing and the wellbore, and the surface equipment is disposed at the wellsite surface and comprises a processor;
    conveying a downhole tool of the CAS within the wellbore while operating the CAS to obtain first log data that includes a second FSLO and a second ZMUD each measured with respect to depth in the wellbore;
    operating the CAS to estimate a third FSLO based on a thickness of the casing, the external diameter, and a transit time for energy emitted by the downhole tool to travel to and from the casing;
    operating the CAS to estimate a third ZMUD based on the predetermined density, an expected impedance in the annulus, a selected one of the first FSLO, the second FSLO, and the third FSLO, and a selected one of the first ZMUD, the second ZMUD;

conveying the downhole tool in a free-pipe (FP) zone of the wellbore while operating the CAS to obtain second log data that includes a fourth FSLO and a fourth ZMUD each measured with respect to depth in the FP zone;

operating the CAS to generate an FSLO graphical interface based on the first FSLO, the second FSLO, the third FSLO, and the fourth FSLO;

operating the CAS to estimate a fifth ZMUD based on the predetermined type and predetermined density of the drilling fluid and a selected one of the first FSLO, the second FSLO, the third FSLO, and the fourth FSLO, wherein the selected one of the first FSLO, the second FSLO, the third FSLO, and the fourth FSLO is selected utilizing the FSLO graphical interface;

operating the CAS to generate a ZMUD graphical interface based on the first ZMUD, the second ZMUD, the third ZMUD, the fourth ZMUD, and the fifth ZMUD; and conveying the downhole tool within the wellbore while operating the CAS to obtain third log data utilizing at least one parameter selected utilizing the ZMUD graphical interface, wherein the third log data includes a final ZMUD measured with respect to depth in the wellbore.

11. The method of claim 10 wherein the first log data is obtained while conveying the downhole tool in a first direction, and wherein the third log data is obtained while conveying the downhole tool in a second direction that is substantially opposite the first direction.

12. The method of claim 11 wherein operating the CAS to obtain the first log data and the third log data comprises operating the downhole tool to obtain pulse-echo measurements.

13. The method of claim 11 wherein operating the CAS to obtain the first log data and the third log data comprises operating the downhole tool to obtain pulse-echo measurements and flexural attenuation measurements.

14. The method of claim 13 further comprising conveying the downhole tool in the FP zone again while operating the CAS to obtain fourth log data that includes a fifth FSLO and a sixth ZMUD each measured with respect to depth in the FP zone, and wherein the FSLO and ZMUD graphical interfaces are generated further based on the fifth FSLO and the sixth ZMUD, respectively.

15. An apparatus, comprising:
surface equipment disposed at a wellsite surface and comprising a processor, wherein a wellbore extending from the wellsite surface comprises a steel casing secured within the wellbore by cement in an annulus between an external diameter of the casing and the wellbore, wherein an amount of drilling fluid fills at least a portion of the casing, and wherein the surface equipment is operable to:
  estimate a first drilling fluid slowness (FSLO) and a first drilling fluid acoustic impedance (ZMUD) based on a type and density of the drilling fluid;
  estimate a second FSLO based on a thickness of the casing, the external diameter, and a transit time for energy emitted by the downhole tool to travel to and from the casing;
  generate an FSLO graphical interface based on the first FSLO and the second FSLO;
  estimate a second ZMUD based on the type and density of the drilling fluid and a selected one of the first FSLO and the second FSLO, wherein the selected one of the first FSLO and the second FSLO is selected utilizing the FSLO graphical interface; and
  generate a ZMUD graphical interface based on the first ZMUD and the second ZMUD; and
a downhole tool operable for conveyance within the drilling fluid inside the wellbore while obtaining log data utilizing at least one parameter selected utilizing the ZMUD graphical interface, wherein the log data includes a final ZMUD measured with respect to depth in the wellbore.

16. The apparatus of claim 15 wherein the log data includes pulse-echo measurements.

17. The apparatus of claim 15 wherein the log data includes pulse-echo measurements and flexural attenuation measurements.

18. The apparatus of claim 15 wherein the log data is first log data and the downhole tool is further operable for conveyance within the drilling fluid inside the wellbore while obtaining second log data that includes a third FSLO and a third ZMUD each measured with respect to depth in the wellbore, and wherein the FSLO and ZMUD graphical interfaces are generated further based on the third FSLO and the third ZMUD, respectively.

19. The apparatus of claim 18 wherein the first log data is obtained while conveying the downhole tool in a first direction, and wherein the second log data is obtained while conveying the downhole tool in a second direction that is substantially opposite the first direction.

20. The apparatus of claim 15 wherein the log data is first log data and the downhole tool is further operable for conveyance within the drilling fluid inside a free-pipe (FP) zone of the wellbore while obtaining second log data that includes a third FSLO and a third ZMUD each measured with respect to depth in the FP zone, and wherein the FSLO and ZMUD graphical interfaces are generated further based on the third FSLO and the third ZMUD, respectively.

* * * * *